United States Patent [19]

Tiefenbrun et al.

[11] Patent Number: 5,222,939
[45] Date of Patent: Jun. 29, 1993

[54] INSTRUMENT AND ASSOCIATED METHOD FOR APPLYING BIOLOGICALLY EFFECTIVE COMPOSITION DURING SURGERY

[76] Inventors: Jonathan Tiefenbrun, 62 Country Rd., Mamaronek, N.Y. 10543; Peter J. Wilk, 185 West End Ave., New York, N.Y. 10023

[21] Appl. No.: 866,814

[22] Filed: Apr. 9, 1992

[51] Int. Cl.$^5$ .............................. A61M 31/00
[52] U.S. Cl. ........................ 604/59; 604/2; 604/57; 604/183; 401/284
[58] Field of Search ............. 604/1, 2, 57–64, 604/183, 191, 181, 187, 218; 401/282, 284, 286

[56] References Cited

U.S. PATENT DOCUMENTS

| | | | |
|---|---|---|---|
| 1,609,640 | 12/1926 | Bell | 604/183 |
| 1,711,352 | 4/1929 | Jeffreys | 604/1 |
| 3,203,455 | 8/1965 | Horabin | 604/183 |
| 3,428,404 | 2/1969 | Cianco | 401/284 |
| 3,749,084 | 7/1973 | Cucchiara | 604/191 |
| 3,948,759 | 4/1976 | Boldul et al. | 604/191 |
| 4,073,293 | 2/1978 | Phillips et al. | 604/183 |
| 4,485,824 | 12/1984 | Koll | 604/1 |
| 4,692,140 | 9/1987 | Olson | 604/35 |
| 4,790,819 | 12/1988 | Li et al. | 604/59 |
| 4,801,263 | 1/1989 | Clark | 604/60 |
| 4,877,037 | 10/1989 | Ko et al. | 604/117 |
| 4,997,371 | 3/1991 | Fischer | 604/311 |

FOREIGN PATENT DOCUMENTS

| | | | |
|---|---|---|---|
| 619625 | 10/1935 | Fed. Rep. of Germany | 604/58 |
| 395472 | 3/1909 | France | 604/58 |
| 1627186 | 2/1991 | U.S.S.R. | 604/181 |

*Primary Examiner*—Ralph Lewis
*Attorney, Agent, or Firm*—R. Neil Sudol; Henry D. Coleman

[57] ABSTRACT

A laparoscopic instrument comprises a receptacle for storing a predetermined amount of a biologically active composition, a mechanical ejector operatively connected to the receptacle for ejecting the predetermined amount of the biologically active composition into a patient's abdomen, and an actuator operatively connected to the ejector for enabling an actuation of the ejector to eject the predetermined amount of the biologically active composition into the patient's abdomen. The laparoscopic instrument includes an elongate hollow shaft.

10 Claims, 1 Drawing Sheet

INSTRUMENT AND ASSOCIATED METHOD FOR APPLYING BIOLOGICALLY EFFECTIVE COMPOSITION DURING SURGERY

BACKGROUND OF THE INVENTION

This invention relates to a laparoscopic instrument. More particularly, this invention relates to an instrument used during a laparoscopic operation for delivering or applying a biologically effective composition to a surface inside a patient. The substance may specifically take the form of a nontoxic biocompatible adhesive or a hemostatic substance.

Laparoscopy involves the piercing of the abdominal wall with a trocar and the insertion of a tubular cannula or trocar sleeve through the perforation. Various instruments may be inserted through the trocar sleeve to perform surgical operations inside the abdomen.

Generally, upon the disposition of the first trocar sleeve so that it traverses the abdominal wall, the abdominal cavity is pressurized to distend the abdominal wall and provide a safety region between the wall and the body organs inside the cavity. Moreover, several perforations are made. One perforation receives a laparoscope which enables visual monitoring of organs and surgical activities inside the abdominal cavity. Other perforations serve for the insertion of different surgical instruments.

Laparoscopic surgery provides several advantages over conventional incision-based surgery. The laparoscopic perforations, in being substantially smaller than the incisions made during conventional operations, are less traumatic to the patient and provide for an accelerated recovery and convalescence. Hospital stays are minimized. Concomitantly, laparoscopic surgery is less time consuming and less expensive than conventional surgery for correcting the same problems.

Frequently, controlled amounts of biologically active or effective compositions, such as coagulating agents, are introduced into the patient's abdomen during a laparoscopic procedure. These compositions must be transferred to the abdominal cavity through the trocar ports or laparoscopic cannulas, like the instrumentation used. Generally, a predetermined amount of a composition is placed on a spatula or other conventional laparoscopic instrument, the distal end of which is then inserted into the patient's abdomen through a trocar port or cannula. This method is delicate and difficult insofar as the tip of the applicator instrument may contact the inner surface of the trocar port or insofar as the biologically active composition may be dropped or otherwise lost during transit to the surgical site.

OBJECTS OF THE INVENTION

An object of the present invention is to provide a laparoscopic instrument for facilitating the application of controlled amounts of biologically active or effective substances to surfaces of internal body organs or prosthetic elements such as patches (e.g., a hernia cover patch) inside a patient's abdomen during a laparoscopic operation.

A more particular object of the present invention is to provide a laparoscopic instrument for applying a biologically effective adhesive to a surface inside a patient during a laparoscopic procedure.

A further particular object of the present invention is to provide a laparoscopic instrument for applying a coagulating agent to a surface inside a patient during a laparoscopic procedure.

Yet another particular object of the present invention is to provide such a laparoscopic instrument which is inexpensive to make and easy to use.

SUMMARY OF THE INVENTION

A laparoscopic instrument comprises, in accordance with a general conceptualization of the present invention, a receptacle for storing a predetermined amount of a biologically active or effective composition, a mechanical ejector operatively connected to the receptacle for ejecting the predetermined amount of the composition into a patient's abdomen, and an actuator operatively connected to the ejector for enabling an actuation of the ejector to eject the predetermined amount of the composition into the patient's abdomen.

The laparoscopic instrument includes an elongate hollow shaft. The ejector may include a push rod extending longitudinally through the shaft, while the receptacle includes a distal end portion of the shaft. This particular embodiment of the invention is particularly efficacious for delivering a hemostatic substance or coagulating agent such as AVATINE TM to a surgical site inside a patient during a laparoscopic instrument procedure. The coagulating agent is stored in the shaft at the distal end thereof distally of the distal end of the push rod. Pursuant to another feature of the present invention, the push rod is provided at its distal end with an enlarged portion functioning like a piston. The piston contacts an inner surface of the shaft.

Alternatively, the elongate shaft is provided with a duct extending from the storage receptacle to a distal end portion of a channel in which a rod with an applicator element at a distal end is slidably disposed. A feeder mechanism is operatively connected to the receptacle for feeding the biologically active composition from the receptacle to the distal end portion of the channel, whereby the applicator element can engage the biologically active composition to apply the biologically active composition to a surface inside the patient.

This embodiment of a laparoscopic instrument in accordance with the present invention is especially adapted to deliver a biologically effective, i.e., nontoxic and biocompatible, adhesive to a subject surface, such as an organ or a prosthetic implant such as a patch. According to another feature of the present invention, the applicator element at the distal end of the rod in this particular embodiment of the invention is a brush.

Pursuant to another feature of the present invention, the feeder mechanism may include a syringe connected to the shaft at the proximal end thereof. Naturally, other kinds of feeding mechanisms such as an electrically driven pump can be employed. The pump can be designed to apply measured charges of a glue to the applicator brush at the distal end of the applicator rod.

A laparoscopic instrument comprises, in accordance with another particular embodiment of the present invention, an elongate hollow shaft, a feeder mechanism operatively connected to the shaft for delivering a predetermined amount of a biologically effective adhesive to a distal end of the shaft, and a cupshaped receptacle at a distal end of the shaft for receiving and temporarily holding a charge of the adhesive and for releasing the charge upon engagement of the cup-shaped receptacle with a surface inside a patient.

As mentioned above, the feeder mechanism may include a syringe attached to the shaft at a proximal end thereof.

A laparoscopic instrument in accordance with the present invention facilitates the application of controlled amounts of biologically active substances to surfaces of internal body organs or prosthetic elements such as patches (e.g., a hernia cover patch) inside a patient's abdomen during a laparoscopic operation. The instrument may be inexpensively fabricated and is easy to use.

A surgical method comprises, in accordance with the present invention, the steps of (a) using a trocar to form a perforation in an external body surface of a patient, (b) disposing a trocar sleeve in the perforation, (c) inserting an elongate instrument through the trocar sleeve so that and distal end of the instrument protrudes into a body cavity of the patient while a proximal end of the instrument remains outside the patient, (d) initially manipulating the proximal end of the instrument, from outside the patient, to eject a biologically active composition from a distal end of the instrument, and (e) additionally manipulating the proximal end of the instrument, from outside the patient, to apply the ejected biologically active composition to an organic tissue surface of the patient inside the body cavity.

According to another feature of the present invention, where the instrument includes an elongate hollow shaft and a rod slidably inserted in the shaft, the step of additionally manipulating includes the step of manipulating the rod from outside the patient to contact the organic tissue surface with a distal end of the rod.

Where the rod is provided at its distal end with a a brush applicator element, the step of additionally manipulating includes the step of manipulating the rod from solitude the patient to contact the organic tissue surface with the brush applicator element.

Where the instrument includes an elongate hollow shaft and a rod slidably inserted in a main channel in the shaft and where the instrument further includes an ancillary channel extending through the shaft in parallel to the main channel, the step f initially manipulating includes the step of manipulating the instrument to push the biologically active composition from a distal end of the ancillary channel into the main channel at a distal end thereof.

According to another feature of the present invention, the biologically active composition is applied to an organic tissue surface by pressing a distal tip of the instrument against the tissue surface.

The biologically active composition may be a hemostatic substance such as AVATINE ™ or a biologically effective adhesive.

DETAILED DESCRIPTION

Figure 1:
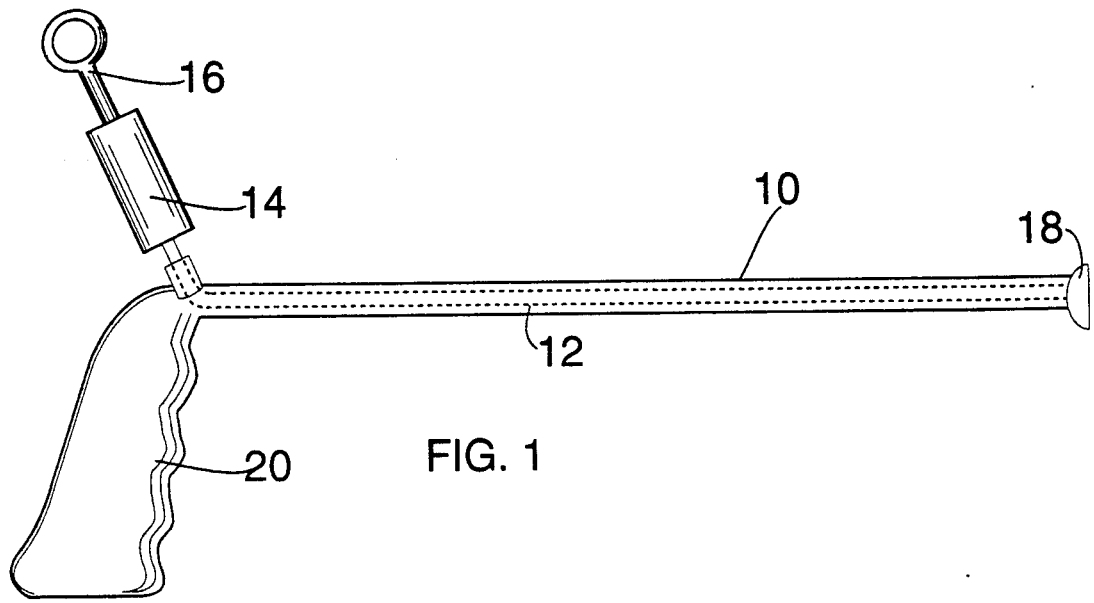
FIG. 1 is a schematic side elevational view of a laparoscopic adhesive delivery instrument in accordance with the present invention.

As illustrated in FIG. 1, a laparoscopic instrument for delivering a charge of a biologically effective, non-toxic and biocompatible adhesive to a desired location inside a patient's abdomen comprises an elongate hollow shaft 10 having a longitudinally extending channel or bore 12. A receptacle or reservoir in the form of a syringe 14 is operatively connected to shaft 10 at the proximal end thereof. Syringe 14 serves as a reservoir or receptacle holding a predetermined amount of the adhesive and is provided with a manually actuatable plunger 16 for pressurizing the adhesive in the syringe to force the adhesive through channel 12 to a distal end of shaft 10.

At its distal end, shaft 10 is provided with a cup-shaped receptacle 18 for receiving and temporarily holding a charge of the adhesive and for releasing the charge upon engagement of the cup-shaped receptacle with a surface inside a patient. Cup-shaped receptacle 18 thus facilitates the delivery of a significantly controllable amount of adhesive to a desired location inside the patient. Receptacle 18 may be made of a flexible material having a memory so that it deforms upon forcible contact with a surface and subsequently returns to its cup shape.

Other feeder mechanisms may be substituted for syringe 14 and plunger 16. For example, a handle 20 at the proximal end of shaft 10 may define a reservoir for receiving a predetermined amount of the adhesive. In addition, a trigger like actuator (not shown) may be attached to shaft 10 and/or handle 20 for exerting a pressurizing force or a pumping action to move a charge of the adhesive through channel 12 to cup-shaped receptacle 18.

Figure 2:
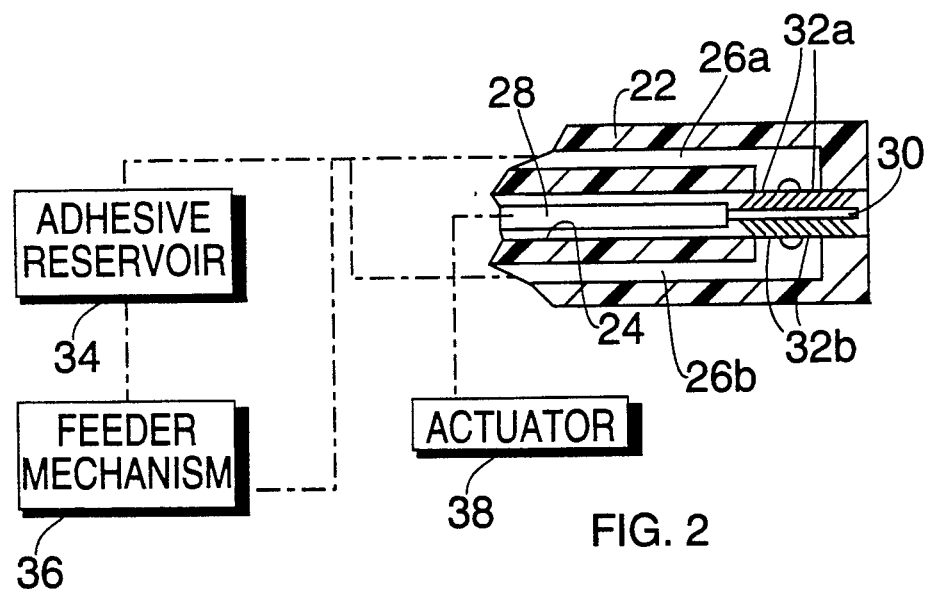
FIG. 2 is partially a block diagram and partially a cross-sectional view of another laparoscopic adhesive applicator or delivery instrument in accordance with the present invention.

As illustrated in FIG. 2, another laparoscopic instrument for delivering or applying a biologically effective, nontoxic and biocompatible adhesive to a desired surgical site inside a patient during a laparoscopic procedure includes an elongate hollow shaft 22 provided with a main channel 24 and a plurality of ancillary channels 26a and 26b. Main channel 24 is longitudinally traversed in part by a rod 28 provided at a distal end with an applicator brush 30. Ancillary channels 26a and 26b have openings 32a and 32b at the distal end of shaft 22.

Ancillary channels 26a and 26b communicate with a reservoir or receptacle 34 which contains a quantity of a biologically effective adhesive, i.e., a nontoxic composition capable of bonding biological tissues to one another and to prosthetic implant devices. A feeder mechanism 36 is operatively connected to reservoir or receptacle 34 for enabling the delivery of a controllable amount of the adhesive through channels 26a and 26b to a distal end of shaft 22.

Upon a feeding of adhesive to applicator brush 28 via channels 26a and 26b and openings 32a and 32b, rod 28 is pushed in the distal direction to eject the adhesive on the applicator brush. These steps are implemented upon an insertion of a distal end of shaft 22 into the abdomen of a patient through a laparoscopic trocar sleeve.

An actuator 38 such as a handle is operatively connected to rod 28 for enabling an actuation of the rod from outside the patient to dispense the adhesive into the patient's abdomen.

Adhesives which may be utilized with the laparoscopic instruments of FIGS. 1 and 2 include cyanoacrylic compositions and fibrin glues or sealants such as TISSUCOL ™ and BERIPLAST ™. The laparoscopic instruments of FIGS. 1 and 2 may each be provided with two reservoirs at a proximal end for separately holding two different chemical components, as well as two longitudinally extending feed channels for enabling a mixing of the two compositions at a distal end of the respective instrument to generate a chemical reaction producing an adhesive composition which will harden and fixate within a characteristic predetermined interval.

Figure 3:
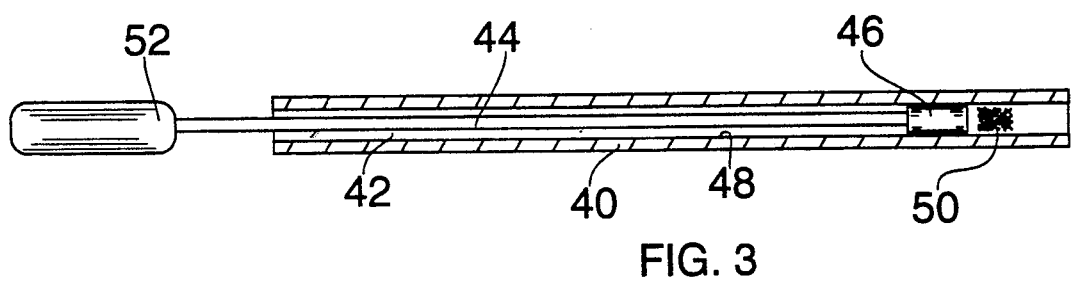
FIG. 3 is a schematic longitudinal cross-sectional view of a laparoscopic instrument for delivering or applying a charge of a hemostatic agent, in accordance with the present invention.

As illustrated in FIG. 3, a laparoscopic instrument for delivering a predetermined amount of a hemostatic substance or coagulating agent inside a patient during a laparoscopic procedure includes an elongate hollow shaft 40 provided with a longitudinally extending channel 42 and an ejector rod 44 at least partially disposed inside the channel. Ejector rod 44 is provided at a distal end with a piston 46 which engages a cylindrical inner wall 48 of shaft 40.

Disposed inside shaft 40 distally of piston 46 is a predetermined charge 50 of a coagulating agent such as AVATINE TM AVATINE TM charge 50 is ejected by a distally directed stroke of rod 44 upon an insertion of a distal end of shaft 40 into the abdomen of a patient through a laparoscopic cannula.

A handle type actuator 52 is operatively connected to ejector rod 44 for enabling a actuation of the rod from outside the patient to precisely eject or dispense the coagulating substance into the patient's abdomen at a desired location.

The laparoscopic instrument of FIG. 3 may be prepackaged and disposable upon the delivery of charge 50 to a surgical site. To that end a plug (not shown) may be inserted in the distal end of channel 42 to hold charge 50 during shipping and storage prior to use.

Although the invention has been described in terms of particular embodiments and applications, one of ordinary skill in the art, in light of this teaching, can generate additional embodiments and modifications without departing from the spirit of or exceeding the scope of the claimed invention. For example, substances other than an adhesive or a hemostatic factor may be precisely and controlled delivered to a desired surgical site inside a patient during a laparoscopic procedure using instruments in accordance with the present invention.

In addition, the dispensing action may effectuated equivalently by controlling a valve at an outlet of a pressurized reservoir of adhesive or other fluidic substance.

Accordingly, it is to be understood that the drawings and descriptions herein are preferred by way of example to facilitate comprehension of the invention and should not be construed to limit the scope thereof.

What is claimed is:

1. A surgical instrument comprising:
    an elongate hollow shaft having a longitudinally extending main channel;
    feeder means for delivering a predetermined amount of a biologically effective adhesive to a distal end of said main channel, said feeder means including a pair of longitudinally extending ancillary channels in said shaft, said ancillary channels communicating at a distal end with a distal end of said main channel;
    mechanical ejector means including a rod slidably inserted through said main channel of said shaft for ejecting said adhesive into a patient upon an insertion of a distal end of said shaft into the patient through a trocar sleeve, said rod being provided at a distal end with an applicator brush
    first actuator means operatively a connected to said rod for enabling an actuation of said ejector means from outside said patient to eject said adhesive into the patient's abdomen; and
    second actuator means operatively connected to said ancillary channels for pushing said adhesive out of said ancillary channels and into said main channel for entrainment by said brush.

2. The instrument defined in claim 1 wherein said second actuator means includes a syringe attached to said shaft at a proximal end thereof, said syringe communicating with said ancillary channels.

3. A surgical method comprising the step of:
    using a trocar to form a perforation in an external body surface of a patient;
    disposing a trocar sleeve in said perforation;
    inserting an elongate instrument through said trocar sleeve so that a distal end of said instrument protrudes into a body cavity of the patient while a proximal end of said instrument remains outside said patient, said distal end of said instrument being provided with a substantially flexible applicator element;
    initially manipulating said proximal end of said instrument, from outside the patient, object a biologically active composition from said distal end of said instrument and
    additionally manipulating said proximal end of said instrument, from outside the patient, to contact, with said flexible applicator element, an organic tissue surface of the patient inside said body cavity so as to spread the ejected biologically active composition along said organic tissue surface.

4. The method defined in claim 3 wherein said instrument includes an elongate hollow shaft and a rod slidably inserted in said shaft, said flexible applicator element being attached to said rod, said step of additionally manipulating including the step of manipulating said rod from outside the patient to contact said organic tissue surface with said flexible applicator element.

5. The method defined in claim 4 wherein said flexible applicator element is a brush applicator element.

6. The method defined in claim 3 wherein said instrument includes an elongate hollow shaft and a rod slidably inserted in a main channel in said shaft, said flexible applicator element being attached to said rod, said instrument further including an ancillary channel extending through said shaft in parallel to said main channel, said step of initially manipulating including the step of manipulating said instrument to push said biologically active composition from a distal end of said ancillary channel into said main channel at a distal end hereof.

7. The method defined in claim 6 wherein said ancillary channel is one of two ancillary channels, further comprising the step of dispensing an ancillary composition from one of said ancillary channels into said main channel at the distal end thereof.

8. The method defined in claim 3 wherein said instrument includes an elongate hollow shaft and a rod slidably inserted in said shaft, said flexible applicator element being arched to said rod, said biologically active composition being stored in said shaft distally of a distal end of said rod, said step of initially manipulating including the step of manipulating said rod from outside the patient to push said biologically active composition from eh distal end of said shaft.

9. The method defined in claim 3 wherein said biologically active composition is a hemostatic substance.

10. The method defined in claim 3 wherein said biologically active composition is a biologically effective adhesive.

* * * * *

UNITED STATES PATENT AND TRADEMARK OFFICE
CERTIFICATE OF CORRECTION

PATENT NO. : 5,222,939
DATED : June 29, 1993
INVENTOR(S) : Jonathan Tiefenbrun and Peter J. Wilk It is certified that error appears in the above-identified patent and that said Letters Patent is hereby corrected as shown below:

Column 3, line 34, delete "a" ( second occurrence); line 37, change "solitude" to --outside--; Line 43, change "step f" to --step of--.

Column 5, line 19, insert --.-- (period) after "TM" (first occurrence); line 48, change "preferred" to --profferred--.

Column 5, line 66, insert --;-- (semi-colon) after "brush".

Column 6, line 23, change "object" to --to eject--; line 15, insert --;-- (semi-colon) after "instrument".

Column 6, line 57, change "arched" to --attached--; line 62, change "eh" to --the--.

Signed and Sealed this

Fourth Day of October, 1994

Attest:

BRUCE LEHMAN

*Attesting Officer*     *Commissioner of Patents and Trademarks*